United States Patent [19]

Buzzetti et al.

[11] Patent Number: 5,639,884

[45] Date of Patent: Jun. 17, 1997

[54] ARYLIDENE-HETEROCYCLIC DERIVATIVES AND PROCESS FOR THEIR PREPARATION

[75] Inventors: Franco Buzzetti, Monza; Silvia Fustinoni, Milan; Maria Gabriella Brasca, Cusago; Sergio Penco, Milan, all of Italy

[73] Assignee: Farmitalia Carlo Erba S.r.l., Milan, Italy

[21] Appl. No.: 400,113

[22] Filed: Mar. 6, 1995

Related U.S. Application Data

[63] Continuation of Ser. No. 988,867, Dec. 10, 1992, abandoned.

[30] Foreign Application Priority Data

Dec. 24, 1991 [GB] United Kingdom ............ 9127401
Jan. 29, 1992 [GB] United Kingdom ............ 9201906
Mar. 24, 1992 [GB] United Kingdom ............ 9206369

[51] Int. Cl.[6] ............. C07D 217/24; A61K 31/47
[52] U.S. Cl. .................................................. 546/142
[58] Field of Search ........................ 546/142; 514/309

[56] References Cited

U.S. PATENT DOCUMENTS

| | | | |
|---|---|---|---|
| 3,472,843 | 10/1969 | Skorcz et al. | 546/270 |
| 3,634,415 | 1/1972 | Zinnes et al. | 546/142 |
| 4,251,609 | 2/1981 | Nonnemacher | 430/9 |
| 4,594,303 | 6/1986 | Horie et al. | 430/59 |
| 5,122,537 | 6/1992 | Buzzetti et al. | 514/510 |
| 5,130,472 | 7/1992 | Buzzetti et al. | 560/252 |

FOREIGN PATENT DOCUMENTS 9113055 4/1991 WIPO.

OTHER PUBLICATIONS

Compte Rendus, vol. 244, pp. 1651–1653, 1957, M. R. Dabard.
J. Het. Chem., vol. 13, pp. 597–599, 1976, I. W. Elliott, et al., "Reduction of 4–Arylidene–1, 3–(2H,4H) Isoquinolinediones".
Journal of Heterocyclic Chemistry, vol. 13, No. 3, Jun. 1976, PROVO US pp. 597–599; I.W. Elliott, "Reduction of 4–arylidene–1,3–(2H,4H) isoquinoliediones", pp. 597,598; compounds 3,4,5. Corresponds to USSN 07/768,259, of record.
Comptes Rendus Hebdomadaines des Seances de L'Academie des sciences, 18 Mar. 1957, montreuil Fr. pp. 1651–1653; Rene Dabard, "Recherches sue les derives de condensation des homophtalimides et des aldehydes aromatiques et heterocycliques". Of record.
Federal Register, vol. 60, No. 135, 1995, pp. 36263–36265, 1995.
I.W. Elliott, Jr. et al, "Reduction of 4–Arylidens . . .", J. Heterocyclic Chem., 13, pp. 597–599 (1976).
T.R. Burke Jr, "Protein–Tyrosine Kinose Inhibitors", Drugs of the Future, 17(2), pp. 119–131, 1992.

Dobrusin, "Chapter 18. Protein Tyrosine Kinases and Cancer", *Annual Reports in Medicinal Chemistry*, vol. 27, pp. 169–178, 1992.
Yoneda, "The Antiproliferative Effects . . .", *Cancer Research*, 51 pp. 4430–4435, 1991.
P. Spence, "Inhibitors of Tyrosine Kinase . . .", TRI Patent Review, pp. 3–9, 1993.
Toi, "Antineoplastic Effects of Erbstation . . .", *Eur. J. Cancer*, vol. 26 No. 6, p. 722–724, 1990.

*Primary Examiner*—C. Warren Ivy
*Assistant Examiner*—D. Margaret M. Mach
*Attorney, Agent, or Firm*—Oblon, Spivak, McClelland, Maier & Neustadt, P.C.

[57] ABSTRACT

The invention relates to compounds of formula

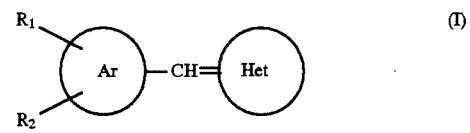

(I)

wherein

Ar is mono- or bicyclic ring system chosen from benzene, naphthalene, tetrahydronaphthalene, quinoline and indole;

Het is

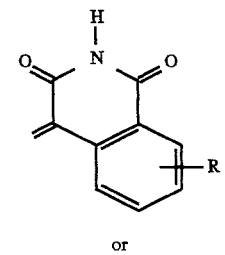

or

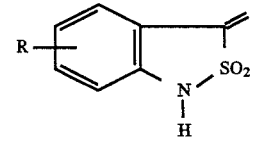

R is hydrogen, halogen, hydroxy, $C_1$–$C_6$ alkoxy, $C_2$–$C_6$ acyloxy, cyano, nitro, amino or —$COOR_3$ in which $R_3$ is hydrogen or $C_1$–$C_6$ alkyl;

$R_1$ is hydrogen, hydroxy, $C_1$–$C_6$ alkyl, $C_1$–$C_6$ alkoxy, $C_2$–$C_6$ acyloxy, cyano, nitro, amino or —$COOR_3$ in which $R_3$ is as defined above;

$R_2$ is hydrogen, halogen, hydroxy or $C_1$–$C_6$ alkyl; and the pharmaceutically acceptable salts thereof, and wherein when at the same time the (Ar)$R_1R_2$ group represents unsubstituted phenyl or 4-chloro-, 4-cyano-, 4-aminoor 3,4-dimethoxy-phenyl and Het is a 4-homophthalimide group, then R is other than hydrogen, which are useful as anti-proliferative agents.

9 Claims, No Drawings

ARYLIDENE-HETEROCYCLIC DERIVATIVES AND PROCESS FOR THEIR PREPARATION

This application is a Continuation of application Ser. No. 07/988,867, filed on Dec. 10, 1992, now abandoned.

The present invention relates to 4-arylidene-homophthalimide and 3-arylidene-2,1-benzisothiazoline-2,2-dioxide derivatives, to a process for their preparation, to pharmaceutical compositions containing them and to their use as therapeutic agents, in particular as tyrosine kinase inhibitors.

4-Arylidene-1,3-(2H,4H)isoquinolinediones are disclosed by J. Het. Chem. 13, 597–9 (1976) and Comptes rendus 244, 1651 (1957). In particular, the former reference describes the catalytic hydrogenation of some 4-arylidene-homophthalimides to afford the corresponding 4-arylmethylhomophthalimide derivatives and the latter reference the synthesis and the polarographic study of products obtained by condensing homophthalimides with aromatic and heterocyclic aldehydes.

The compounds provided by the present invention are new with the exception of some 4-benzylidene compounds, which are disclosed in J. Heterocycl. Chem. 13, 597 (1976) and Comptes rendus 244, 1651 (1957). However, no therapeutic utility is described for said known compounds in the above prior reference.

Accordingly, the present invention provides new arylidene derivatives having the following formula (I)

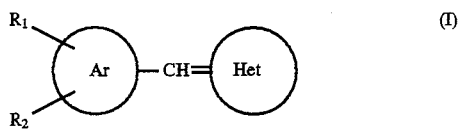

(I)

wherein

Ar is a mono- or bicyclic ring system chosen from benzene, naphthalene, tetrahydronaphthalene, quinoline and indole;

Het is

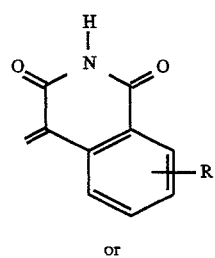

or

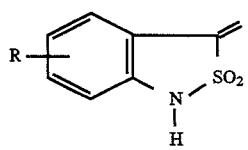

R is hydrogen, halogen, hydroxy, $C_1$–$C_6$ alkoxy, $C_2$–$C_6$ acyloxy, cyano, nitro, amino or —$COOR_3$ in which $R_3$ is hydrogen or $C_1$–$C_6$ alkyl;

$R_1$ is hydrogen, hydroxy, $C_1$–$C_6$ alkyl, $C_1$–$C_6$ alkoxy, $C_2$–$C_6$ acyloxy, cyano, nitro, amino or —$COOR_3$ in which $R_3$ is as defined above;

$R_2$ is hydrogen, halogen, hydroxy or $C_1$–$C_6$ alkyl; and the pharmaceutically acceptable salts thereof, and wherein, when at the same time the (Ar)$R_1R_2$ group represents unsubstituted phenyl or 4-chloro-, 4-cyano-, 4-amino- or 3,4-dimethoxy-phenyl and Het is a homophthalimide group, then R is other than hydrogen.

Compounds falling within the scope of general formula (I) above are all the possible isomers, stereoisomers, in particular Z and E isomers and their mixtures, and the metabolites and the metabolic precursors or bioprecursors (otherwise known as pro-drugs) of the compounds of formula (I).

The alkyl, acyl and alkoxy groups may be branched or straight chain groups.

A $C_1$–$C_6$ alkyl group is preferably a $C_1$–$C_4$ alkyl group, e.g. methyl, ethyl, propyl, isopropyl, butyl, sec-butyl or tert-butyl, in particular methyl or ethyl.

A $C_1$–$C_6$ alkoxy group is preferably a $C_1$–$C_4$ alkoxy group, in particular methoxy, ethoxy, propoxy or isopropoxy.

A halogen is preferably chlorine, bromine or fluorine, in particular chlorine.

A $C_2$–$C_6$ acyloxy group is preferably a $C_2$–$C_4$ acyloxy group, typically acetyloxy or propionyloxy.

A tetrahydronaphthalene group is preferably a 5',6',7',8'-tetrahydronaphth-2'-yl, a 5',6',7',8'-tetrahydronaphth-1'-yl, a 1',2',3',4'-tetrahydronaphth-1'-yl or a 1',2',3',4'-tetrahydronaphth-2'-yl group, being the 5',6',7',8'-tetrahydronaphth-2'-yl and 5',6',7',8'-tetrahydronaphth-1'-yl groups the most preferred.

The 3-methylene-2,1-benzoisothiazoline-2,2-dioxide is preferably substituted by R at the 5-position. The 4-methylenehomophthalimide group is preferably substituted at the 6-position.

Each of the substituents $R_1$ and $R_2$ and the 3-methylene-2,1-benzoisothiazoline-2,2-dioxide group or the 4-methylene-homophthalimide group respectively may be independently on either of the aryl or heteroaryl moieties of the Ar group where Ar denotes naphthalene, quinoline or indole. Only the benzene moiety is preferably substituted when Ar is a tetrahydronaphthalene group.

Preferred substitution patterns are as follows:

i) When Ar is benzene, i.e. phenyl, preferably the $R_1$ and $R_2$ substituents are located at the 3'- and/or 4'-positions.

ii) When Ar is naphthalene, both the $R_1$ and $R_2$ substituents and the 3-methylene-2,1-benzoisothiazoline-2,2-dioxide or 4-methylene-homophthalimide group respectively are preferably on the same benzene moiety. Preferably Ar is a 1'-naphthyl or 2'-naphthyl group. Preferably the 1'-naphthyl group is substituted by the $R_1$ and $R_2$ groups at the 3'- and/or 4'-positions. Preferably the 2'-naphthyl group is substituted by the $R_1$ and $R_2$ groups at the 1'- and/or 4'-positions.

iii) When Ar is 5',6',7',8'-tetrahydronaphthalene, it is preferably linked at the 1'- or 2'-position to the 3-methylene-2,1-benzoisothiazoline-2,2-dioxide or 4-methylene-homophthalimide group, respectively. Preferably the 1'-linked group is substituted by the $R_1$ and $R_2$ groups at the 3'- and/or 4'-positions. Preferably the 2'-linked group is substituted by the $R_1$ and $R_2$ groups at the 1'- and/or 4'-positions.

When Ar is 1',2',3',4'-tetrahydronaphthalene, it is preferably a 1',2',3',4'-tetrahydronaphth-1'-yl or 1',2',3',4'-tetrahydronaphth-2'-yl group.

Preferably the 1',2',3',4'-tetrahydronaphth-1'-yl group is substituted by the $R_1$ and $R_2$ groups at the 3'- and/or 4'-positions Preferably the 1',2',3',4'-tetrahydronaphth-2'-yl group is substituted by the $R_1$ and $R_2$ groups at the 1'- and/or 4'-positions.

When Ar is 1,2,3,4-tetrahydronaphthalene, it is preferably a 1'-tetralyl or 2'-tetralyl group.

Preferably the 1'-tetralyl group is substituted by the $R_1$ and $R_2$ groups at the 3'- and/or 4'-positions. Preferably the 2'-tetralyl group is substituted by the $R_1$ and $R_2$ groups at the 1'- and/or 4'-positions.

iv) When Ar is quinoline, the 3-methylene-2,1-benzoisothiazoline-2,2-dioxide or the 4-methylene-homophthalimide group, respectively, is preferably attached to the 4'- or 5'-position of the quinolyl group and $R_1$ and $R_2$ are preferably on the same aryl or heteroaryl moiety of said condensed ring system.

Preferably the 4'-quinolyl and the 5'-quinolyl groups are substituted by the $R_1$ and $R_2$ groups at the 7'- and/or 8'-positions.

v) When Ar is indole, the 3-methylene-2,1-benzoisothiazoline-2,2-dioxide or the 4-methylene-homophthalimide group, respectively, is preferably attached to the pyrrole moiety and the $R_1$ and $R_2$ are preferably on the benzene moiety of said condensed ring system. Preferably Ar is a 3'-indolyl group. Preferably the indolyl group is substituted by the $R_1$ and $R_2$ groups at the 5'- and/or 6'-positions.

Of course only one of the substituents $R_1$, $R_2$ and 3-methylene-2,1-benzoisothiazoline-2,2-dioxide or 4-methylene-homophthalimide group respectively, can be linked to the same carbon atom of the Ar mono- or bicyclic ring system. When one of R and $R_1$ is cyano, amino or a group $COOR_3$ as defined above, then the other has preferably a different meaning.

Pharmaceutically acceptable salts of the compounds of the invention include acid addition salts, with inorganic, e.g. nitric, hydrochloric, hydrobromic, sulphuric, perchloric and phosphoric acids, or organic, e.g. acetic, propionic, glycolic, lactic, oxalic, malonic, malic, maleic, tartaric, citric, benzoic, cinnamic, mandelic and salicylic acids, and salts with inorganic, e.g. alkali metal, especially sodium or potassium, bases or alkaline-earth metal, especially calcium or magnesium bases, or with organic bases, e.g. alkylamines, preferably triethylamine.

As stated above, the present invention also includes within its scope pharmaceutically acceptable bio-precursors (otherwise known as pro-drugs) of the compounds of formula (I), i.e. compounds which have a different formula to formula (I) above, but which nevertheless upon administration to a human being are converted directly or indirectly in vivo into a compound of formula (I).

A preferred class of new compounds according to the present invention is therefore the compounds of formula (I), wherein subject to the above proviso:

Ar is a mono- or bicyclic ring system chosen from benzene, naphthalene, 5',6',7',8'-tetrahydronaphthalene, quinoline and indole;

Het is as defined above;

R is hydrogen, hydroxy, nitro or amino;

$R_1$ is hydrogen, hydroxy, cyano, nitro or amino;

$R_2$ is hydrogen or hydroxy; and the pharmaceutically acceptable salts thereof.

Accordingly, more preferred are the compounds of formula (I), wherein subject to the above proviso:

Ar is benzene, naphthalene, 5',6',7',8'-tetrahydronaphthalene, quinoline or indole;

Het is as defined above;

each of R, $R_1$ and $R_2$, independently, is hydrogen or hydroxy, and the pharmaceutically acceptable salts thereof.

Examples of specific compounds of the invention are the following compounds which, when appropriate, may be either Z- or E-diastereomers or Z,E-mixtures of said diastereomers:

4-(4'-hydroxyphenyl)methylenehomophthalimide;
4-(3',4'-dihydroxyphenyl)methylenehomophthalimide;
4-(3'-hydroxyphenyl)methylenehomophthalimide;
6-hydroxy-4-phenylmethylenehomophthalimide;
6-hydroxy-4-(4'-hydroxyphenyl)methylenehomophthalimide;
6-hydroxy-4-(3'-hydroxyphenyl)methylenehomophthalimide;
6-hydroxy-4-(3',4'-dihydroxyphenyl)methylenehomophthalimide;
4-(1'-naphthyl)-methylenehomophthalimide;
4-(4'-hydroxy-1'-naphthyl)-methylenehomophthalimide;
4-(3'-hydroxy-1'-naphthyl)-methylenehomophthalimide;
4-(3',4'-dihydroxy-1'-naphthyl)-methylenehomophthalimide;
6-hydroxy-4-(1'-naphthyl)-methylenehomophthalimide;
6-hydroxy-4-(4'-hydroxy-1'-naphthyl)-methylenehomophthalimide;
6-hydroxy-4-(3'-hydroxy-1'-naphthyl)-methylenehomophthalimide;
6-hydroxy-4-(3',4'-dihydroxy-1'-naphthyl)-methylenehomophthalimide;
4-(2'-naphthyl)-methylenehomophthalimide;
4-(1'-hydroxy-2'-naphthyl)-methylenehomophthalimide;
4-(4'-hydroxy-2'-naphthyl)-methylenehomophthalimide;
4-(1',4'-dihydroxy-2'-naphthyl)-methylenehomophthalimide;
6-hydroxy-4-(2'-naphthyl)-methylenehomophthalimide;
6-hydroxy-4-(1'-hydroxy-2'-naphthyl)-methylenehomophthalimide;
6-hydroxy-4-(4'-hydroxy-2'-naphthyl)-methylenehomophthalimide;
6-hydroxy-4-(1',4'-dihydroxy-2'-naphthyl)-methylenehomophthalimide;
4-(5',6',7',8'-tetrahydronaphth-1'-yl)-methylenehomophthalimide;
4-(4'-hydroxy-5',6',7',8'-tetrahydronaphth-1'-yl)-methylenehomophthalimide;
4-(3'-hydroxy-5',6',7',8'-tetrahydronaphth-1'-yl)-methylenehomophthalimide;
4-(3',4'-dihydroxy-5',6',7',8'-tetrahydronaphth-1'-yl)-methylenehomophthalimide;
6-hydroxy-4-(5',6',7',8'-tetrahydronaphth-1'-yl)-methylenehomophthalimide;
6-hydroxy-4-(4'-hydroxy-5',6',7',8'-tetrahydronaphth-1'-yl)-methylenehomophthalimide;
6-hydroxy-4-(3'-hydroxy-5',6',7',8'-tetrahydronaphth-1'-yl)-methylenehomophthalimide;
6-hydroxy-4-(3',4'-dihydroxy-5',6',7',8'-tetrahydronaphth-1'-yl)-methylenehomophthalimide;
4-(5',6',7',8'-tetrahydronaphth-2'-yl)-methylenehomophthalimide;
4-(1'-hydroxy-5',6',7',8'-tetrahydronaphth-2'-yl)-methylenehomophthalimide;
4-(4'-hydroxy-5',6',7',8'-tetrahydronaphth-2'-yl)-methylenehomophthalimide;
4-(1',4'-dihydroxy-5',6',7',8'-tetrahydronaphth-2'-yl)-methylenehomophthalimide;
6-hydroxy-4-(5',6',7',8'-tetrahydronaphth-2'-yl)-methylenehomophthalimide;

6-hydroxy-4-(1'-hydroxy-5',6',7',8'-tetrahydronaphth-2'-yl)-methylenehomophthalimide;
6-hydroxy-4-(4'-hydroxy-5',6',7',8'-tetrahydronaphth-2'-yl)-methylenehomophthalimide;
6-hydroxy-4-(1',4'-dihydroxy-5',6',7',8'-tetrahydronaphth-2'-yl)-methylenehomophthalimide;
4-(4'-quinolyl)-methylenehomophthalimide;
4-(8'-hydroxy-4'-quinolyl)-methylenehomophthalimide;
4-(7'-hydroxy-4'-quinolyl)-methylenehomophthalimide;
4-(7',8'-dihydroxy-4'-quinolyl)-methylenehomophthalimide;
6-hydroxy-4-(4'-quinolyl)-methylenehomophthalimide;
6-hydroxy-4-(8'-hydroxy-4'-quinolyl)-methylenehomophthalimide;
6-hydroxy-4-(7'-hydroxy-4'-quinolyl)-methylenehomophthalimide;
6-hydroxy-4-(7',8'-dihydroxy-4'-quinolyl)-methylenehomophthalimide;
4-(5'-quinolyl)-methylenehomophthalimide;
4-(8'-hydroxy-5'-quinolyl)-methylenehomophthalimide;
4-(7'-hydroxy-5'-quinolyl)-methylenehomophthalimide;
4-(7',8'-dihydroxy-5'-quinolyl)-methylenehomophthalimide;
6-hydroxy-4-(5'-quinolyl)-methylenehomophthalimide;
6-hydroxy-4-(8'-hydroxy-5'-quinolyl)-methylenehomophthalimide;
6-hydroxy-4-(7'-hydroxy-5'-quinolyl)-methylenehomophthalimide;
6-hydroxy-4-(7',8'-dihydroxy-5'-quinolyl)-methylenehomophthalimide;
4-(3'-indolyl)-methylenehomophthalimide;
4-(5'-hydroxy-3'-indolyl)-methylenehomophthalimide;
4-(6'-hydroxy-3'-indolyl)-methylenehomophthalimide;
4-(5',6'-dihydroxy-3'-indolyl)-methylenehomophthalimide;
6-hydroxy-4-(3'-indolyl)-methylenehomophthalimide;
6-hydroxy-4-(5'-hydroxy-3'-indolyl)-methylenehomophthalimide;
6-hydroxy-4-(6'-hydroxy-3'-indolyl)-methylenehomophthalimide;
6-hydroxy-4-(5',6'-dihydroxy-3'-indolyl)-methylenehomophthalimide;
3-phenylmethylene-2,1-benzisothiazoline-2,2-dioxide;
3-(4'-hydroxyphenyl)methylene-2,1-benzisothiazoline-2,2-dioxide;
3-(3',4'-dihydroxyphenyl)methylene-2,1-benzisothiazoline-2,2-dioxide;
3-(3'-hydroxyphenyl)methylene-2,1-benzisothiazoline-2,2-dioxide;
5-hydroxy-3-phenylmethylene-2,1-benzisothiazoline-2,2-dioxide;
5-hydroxy-3-(4'-hydroxyphenyl)methylene-2,1-benzisothiazoline-2,2-dioxide;
5-hydroxy-3-(3'-hydroxyphenyl)methylene-2,1-benzisothiazoline-2,2-dioxide;
5-hydroxy-3-(3',4'-dihydroxyphenyl)methylene-2,1-benzisothiazoline-2,2-dioxide;
3-(1'-naphthyl)methylene-2,1-benzisothiazoline-2,2-dioxide;
3-(3'-hydroxy-1'-naphthyl)methylene-2,1-benzisothiazoline-2,2-dioxide;
3-(4'-hydroxy-1'-naphthyl)methylene-2,1-benzisothiazoline-2,2-dioxide;
3-(3',4'-dihydroxy-1'-naphthyl))methylene-2,1-benzisothiazoline-2,2-dioxide;
5-hydroxy-3-(1'-naphthyl)methylene-2,1-benzisothiazoline-2,2-dioxide;
5-hydroxy-3-(3'-hydroxy-1'-naphthyl)methylene-2,1-benzisothiazoline-2,2-dioxide;
5-hydroxy-3-(4'-hydroxy-1'-naphthyl)methylene-2,1-benzisothiazoline-2,2-dioxide;
5-hydroxy-3-(3',4'-dihydroxy-1'-naphthyl)methylene-2,1-benzisothiazoline-2,2-dioxide;
3-(2'-naphthyl)methylene-2,1-benzisothiazoline-2,2-dioxide;
3-(1'-hydroxy-2'-naphthyl)methylene-2,1-benzisothiazoline-2,2-dioxide;
3-(4'-hydroxy-2'-naphthyl)methylene-2,1-benzisothiazoline-2,2-dioxide;
3-(1',4'-dihydroxy-2'-naphthyl)methylene-2,1-benzisothiazoline-2,2-dioxide;
5-hydroxy-3-(2'-naphthyl)methylene-2,1-benzisothiazoline-2,2-dioxide;
5-hydroxy-3-(1'-hydroxy-2'-naphthyl)methylene-2,1-benzisothiazoline-2,2-dioxide;
5-hydroxy-3-(4'-hydroxy-2'-naphthyl)methylene-2,1-benzisothiazoline-2,2-dioxide;
5-hydroxy-3-(1',4'-dihydroxy-2'-naphthyl)methylene-2,1-benzisothiazoline-2,2-dioxide;
3-(5',6',7',8'-tetrahydronaphth-1'-yl)methylene-2,1-benzisothiazoline-2,2-dioxide;
3-(4'-hydroxy-5',6',7',8'-tetrahydronaphth-1'-yl)methylene-2,1-benzisothiazoline-2,2-dioxide;
3-(3'-hydroxy-5',6',7',8'-tetrahydronaphth-1'-yl)methylene-2,1-benzoisothiazoline-2,2-dioxide;
3-(3',4'-dihydroxy-5',6',7',8'-tetrahydronaphth-1'-yl)methylene-2,1-benzisothiazoline-2,2-dioxide;
3-(5',6',7',8'-tetrahydronaphth-2'-yl)methylene-2,1-benzisothiazoline-2,2-dioxide;
3-(1'-hydroxy-5',6',7',8'-tetrahydronaphth-2'-yl)methylene-2,1-benzisothiazoline-2,2-dioxide;
3-(4'-hydroxy-5',6',7',8'-tetrahydronaphth-2'-yl)methylene-2,1-benzisothiazoline-2,2-dioxide;
3-(1',4'-dihydroxy-5',6',7',8'-tetrahydronaphth-2'-yl)methylene-2,1-benzisothiazoline-2,2-dioxide;
3-(4'-quinolyl)methylene-2,1-benzisothiazoline-2,2-dioxide;
3-(8'-hydroxy-4'-quinolyl)methylene-2,1-benzisothiazoline-2,2-dioxide;
3-(7'-hydroxy-4'-quinolyl)methylene-2,1-benzisothiazoline-2,2-dioxide;
3-(7',8'-dihydroxy-4'-quinolyl)methylene-2,1-benzisothiazoline-2,2-dioxide;
3-(5'-quinolyl)methylene-2,1-benzisothiazoline-2,2-dioxide;
3-(8'hydroxy-5'-quinolyl)methylene-2,1-benzisothiazoline-2,2-dioxide;
3-(7'-hydroxy-5'-quinolyl)methylene-2,1-benzisothiazoline-2,2-dioxide;
3-(7',8'-dihydroxy-5'-quinolyl)methylene-2,1-benzisothiazoline-2,2-dioxide;
5-hydroxy-3-(4'-quinolyl)methylene-2,1-benzisothiazoline-2,2-dioxide;

5-hydroxy-3-(8'-hydroxy-4'-quinolyl)methylene-2,1-benzisothiazoline-2,2-dioxide;

5-hydroxy-3-(7'-hydroxy-4'-quinolyl)methylene-2,1-benzisothiazoline-2,2-dioxide;

5-hydroxy-3-(7',8'-dihydroxy-4'-quinolyl)methylene-2,1-benzisothiazoline-2,2-dioxide;

5 hydroxy-3-(5'-quinolyl)methylene-2,1-benzisothiazoline-2,2-dioxide;

5-hydroxy-3-(8'-hydroxy-5'-quinolyl)methylene-2,1-benzisothiazoline-2,2-dioxide;

5-hydroxy-3-(7'-hydroxy-5'-quinolyl)methylene-2,1-benzisothiazoline-2,2-dioxide;

5-hydroxy-3-(7',8'-dihydroxy-5'-quinolyl)methylene-2,1-benzisothiazoline-2,2-dioxide;

3-(3'-indolyl)methylene-2,1-benzisothiazoline-2,2-dioxide;

3-(5'-hydroxy-3'-indolyl)methylene-2,1-benzisothiazoline-2,2-dioxide;

3-(6'-hydroxy-3'-indolyl)methylene-2,1-benzisothiazoline-2,2-dioxide;

3-(5',6'-dihydroxy-3'-indolyl)methylene-2,1-benzisothiazoline-2,2-dioxide;

5-hydroxy-3-(3'-indolyl)methylene-2,1-benzisothiazoline-2,2-dioxide;

5-hydroxy-3-(5'-hydroxy-3'-indolyl)methylene-2,1-benzisothiazoline-2,2-dioxide;

5-hydroxy-3-(6'-hydroxy-3'-indolyl)methylene-2,1-benzisothiazoline-2,2-dioxide; and 5-hydroxy-3-(5',6'-dihydroxy-3'-indolyl)methylene-2,1-benzisothiazoline-2,2-dioxide; and, if the case, the pharmaceutically acceptable salts thereof.

A further object of the present invention is to provide a pharmaceutical composition comprising a pharmaceutically acceptable carrier and/or diluent and, as an active principle, a compound of formula (IA)

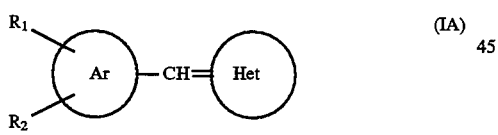

wherein

Ar is a mono- or bicyclic ring system chosen from benzene, naphthalene, tetrahydronaphthalene, quinoline and indole;

Het is

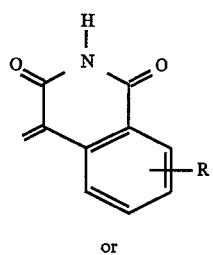

or

-continued

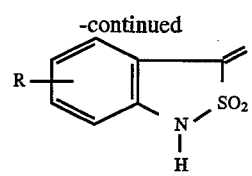

R is hydrogen, halogen, hydroxy, $C_1$–$C_6$ alkoxy, $C_2$–$C_6$ acyloxy, cyano, nitro, amino or —$COOR_3$ in which $R_3$ is hydrogen or $C_1$–$C_6$ alkyl;

$R_1$ is hydrogen, hydroxy, $C_1$–$C_6$ alkyl, $C_1$–$C_6$ alkoxy, $C_2$–$C_6$ acyloxy, cyano, nitro, amino or —$COOR_3$ in which $R_3$ is as defined above;

$R_2$ is hydrogen, halogen, hydroxy or $C_1$–$C_6$ alkyl; or a pharmaceutically acceptable salt thereof.

A further object of the present invention is to provide 4-arylidene-1,3-(2H,4H)isoquinolinediones, i.e. 4-arylidene-homophthalimides, and 3-arylidene-2,1-benzisothiazoline-2,2-dioxides having the general formula (IA), as defined above, or a pharmaceutically acceptable salt thereof for use as an active therapeutic substance, in particular as tyrosine kinase inhibitors in the treatment of cancer, psoriasis, leukemia and other pathological proliferative conditions as herein described.

Object of the present invention is also the use of a compound of formula (IA), as defined above, or a pharmaceutically acceptable salt thereof, for the manufacture of a medicament for use as tyrosine kinase inhibitor, in the treatment of a pathological state as herein described.

Both the new compounds of formula (I) and the known ones of formula (IA) are hereafter referred to as the "active compounds" and as the "compounds of the invention".

From the above it is evident that the new compounds of formula (I) are encompassed by formula (IA) above. Preferred classes of compounds of formula (IA) are, not subject to the above proviso, the preferred types of compounds of formula (I) described above.

Preferred compounds for use as active therapeutic substances or as active ingredients in the preparation of a pharmaceutical composition, according to the invention, are the compounds of formula (IA), wherein Ar is a mono- or bicyclic ring system chosen from benzene, naphthalene, 5,6,7,8-tetrahydronaphthalene, quinoline and indole;

Het is as defined above;

R is hydrogen, hydroxy, nitro or amino;

$R_1$ is hydrogen, hydroxy, cyano, nitro or amino;

$R_2$ is hydrogen or hydroxy; or a pharmaceutically acceptable salt thereof.

Accordingly, more preferred are the compounds of formula (IA), wherein

Ar is benzene, naphthalene, 5,6,7,8-tetrahydronaphthalene, quinoline or indole;

Het is as defined above;

each of R, $R_1$ and $R_2$, independently, is hydrogen or hydroxy, and the pharmaceutically acceptable salt thereof.

Examples of preferred compounds of the invention for use as active therapeutic substances or as active ingredients in the preparation of a pharmaceutical composition according to the invention are the following:

4-phenylmethylenehomophthalimide;

4-(4'-hydroxyphenyl)methylenehomophthalimide;

4-(3',4'-dihydroxyphenyl)methylenehomophthalimide;

4-(3'-hydroxyphenyl)methylenehomophthalimide;
6-hydroxy-4-phenylmethylenehomophthalimide;
6-hydroxy-4-(4'-hydroxyphenyl)methylenehomophthalimide;
6-hydroxy-4-(3'-hydroxyphenyl)methylenehomophthalimide;
6-hydroxy-4-(3',4'-dihydroxyphenyl)methylenehomophthalimide;
4-(1'-naphthyl)-methylenehomophthalimide;
4-(4'-hydroxy-1'-naphthyl)-methylenehomophthalimide;
4-(3'-hydroxy-1'-naphthyl)-methylenehomophthalimide;
4-(3',4'-dihydroxy-1'-naphthyl)-methylenehomophthalimide;
6-hydroxy-4-(1'-naphthyl)-methylenehomophthalimide;
6-hydroxy-4-(4'-hydroxy-1'-naphthyl)-methylenehomophthalimide;
6-hydroxy-4-(3'-hydroxy-1'-naphthyl)-methylenehomophthalimide;
6-hydroxy-4-(3',4'-dihydroxy-1'-naphthyl)-methylenehomophthalimide;
4-(2'-naphthyl)-methylenehomophthalimide;
4-(1'-hydroxy-2'-naphthyl)-methylenehomophthalimide;
4-(1',4'-hydroxy-2'-naphthyl)-methylenehomophthalimide;
4-(1',4'-dihydroxy-2'-naphthyl)-methylenehomophthalimide;
6-hydroxy-4-(2'-naphthyl)-methylenehomophthalimide;
6-hydroxy-4-(14O-hydroxy-2'-naphthyl)-methylenehomophthalimide;
6-hydroxy-4-(4'-hydroxy-2'-naphthyl)-methylenehomophthalimide;
6-hydroxy-4-(1',4'-dihydroxy-2'-naphthyl)-methylenehomophthalimide;
4-(5',6',7',8'-tetrahydronaphth-1'-yl)-methylenehomophthalimide;
4-(4'-hydroxy-5',6',7',8'-tetrahydronaphth-1'-yl)-methylenehomophthalimide;
4-(3'-hydroxy-5',6',7',8'-tetrahydronapth-1'-yl)-methylenehomophthalamide;
4-(3',4'-dihydroxy-5',6',7',8'-tetrahydronaphth-1'-yl)-methylenehomophthalimide;
6-hydroxy-4-(5',6',7',8'-tetrahydronaphth-1'-yl)-methylenehomophthalimide;
6-hydroxy-4-(4'-hydroxy-5',6',7',8'-tetrahydronaphth-1'-yl)-methylenenomophthalamide;
6-hydroxy-4-(3'-hydroxy-5',6',7',8'-tetrahydronaphth-1'-yl)-methylenehomophthalimide;
6-hydroxy-4-(3',4'-dihydroxy-5',6',7',8'-tetrahydronaphth-1'-yl)-methylenehomophthalimide;
4-(5',6',7',8'-tetrahydronapth-2'-yl)-methylenehomophthalimide;
4-(1'-hydroxy-5',6',7',8'-tetrahydronaphth-2'-yl)-methylenehomophthalimide;
4-(4'-hydroxy-5',6',7',8'-tetrahydronaphth-2'-yl)-methylenehomophthalimide;
4-(1',4'-dihydroxy-5',6',7',8'-tetrahydronaphth-2'-yl)-methylenehomophthalimide;
6-hydroxy-4-(5',6',7',8'-tetrahydronaphth-2'-yl)-methylenehomophthalimide;
6-hydroxy-4-(1'-hydroxy-5',6',7',8'-tetrahydronaphth-2'-yl)methylenehomophthalimide;
6-hydroxy-4-(4'-hydroxy-5',6',7',8'-tetrahydronaphth-2'-yl)-methylenehomophthalimide;
6-hydroxy-4-(1',4'-dihydroxy-5',6',7',8'-tetrahydronaphth-2'-yl)methylenehomophthalimide;
4-(4'-quinolyl)-methylenehomophthalimide;
-(8'-hydroxy-4'-quinolyl)-methylenehomophthalimide;
4-(7'-hydroxy-4'-quinolyl)-methylenehomophthalimide;
6-hydroxy-4-(7',8'-dihydroxy-4'-quinolyl)-methylenehomophthalimide;
6-hydroxy-4-(4'-quinolyl)-methylenehomophthalimide;
6-hydroxy-4-(8'-hydroxy-4'-quinolyl)-methylenehomophthalimide:
6-hydroxy-4-(7'-hydroxy-4'-quinolyl)-methylenehomophthalimide;
6-hydroxy-4-(7',8'-dihydroxy-4'-quinolyl)-methylenehomophthalimide;
4-(5'-quinolyl)-methylenehomophthalimide;
4-(8'-hydroxy-5'-quinolyl)-methylenehomophthalimide;
4-(7'-hydroxy-5'-quinolyl)-methylenehomophthalimide;
4-(7',8'-dihydroxy-5'-quinolyl)-methylenehomophthalimide;
6-hydroxy-4-(5'-quinolyl)-methylenehomophthalimide;
6-hydroxy-4-(8'-hydroxy-5'-quinolyl)-methylenehomophthalimide;
6-hydroxy-4-(7'-hydroxy-5'-quinolyl)-methylenehomophthalimide;
6-hydroxy-4-(7',8'-dihydroxy-5'-quinolyl-methylenehomophthalimide;
4-(3'-indolyl)-methylenehomophthalimide;
4-(5'-hydroxy-3'-indolyl)-methylenehomophthalimide;
4-(6'-hydroxy-3'-indolyl)-methylenehomophthalimide;
4-(5',6'-dihydroxy-3'-indolyl)-methylenehomophthalimide;
6-hydroxy-4-(3'-indolyl)-methylenehomophthalimide;
6-hydroxy-4-(5'-hydroxy-3'-indolyl)-methylenehomophthalimide;
6-hydroxy-4-(6'-hydroxy-3'-indolyl)-methylenehomophthalimide;
6-hydroxy-4-(5',6'-dihydroxy-3'-indolyl)-methylenehomophthalimide;
3-phenylmethylene-2,1-benzisothiazoline-2,2-dioxide;
3-(4'-hydroxyphenyl)methylene-2,1-benzisothiazoline-2,2-dioxide;
3-(3',4'-dihydroxyphenyl)methylene-2,1-benzisothiazoline-2,2-dioxide;
3-(3'-hydroxyphenyl)methylene-2,1-benzisothiazoline-2,2-dioxide;
5-hydroxy-3-(1'-phenyl)methylene-2,1-benzisothiazoline-2,2-dioxide;
5-hydroxy-3-(4'-hydroxyphenyl)methylene-2,1-benzisothiazoline-2,2-dioxide;
5-hydroxy-3-(3'-hydroxyphenyl)methylene-2,1-benzisothiazoline-2,2-dioxide;
5-hydroxy-3-(3',4'-dihydroxyphenyl)methylene-2,1-benzisothiazoline-2,2-dioxide;
3-(1'-naphthyl)methylene-2,1-benzisothiazoline-2,2-dioxide;
3-(3'-hydroxy-1'-naphthyl)methylene-2,1-benzisothiazoline-2,2-dioxide;
3-(4'-hydroxy-1'-naphthyl)methylene-2,1-benzisothiazoline-2,2-dioxide;

3-(3',4'-dihydroxy-1'-naphthyl))methylene-2,1-benzisoic thiazoline-2,2-dioxide;

5-hydroxy-3-(1'-naphthyl)methylene-2,1-benzisothiazoline-2,2-dioxide;

5-hydroxy-3-(3'-hydroxy-1'-naphthyl)methylene-2,1-benzisothiazoline-2,2-dioxide;

5-hydroxy-3-(4'-hydroxy-1'-naphthyl)methylene-2,1-benzisothiazoline-2,2-dioxide;

5-hydroxy-3-(3',4'-dihydroxy-1'-naphthyl)methylene-2,1-benzisothiazoline-2,2-dioxide;

3-(2'-naphthyl)methylene-2,1-benzisothiazoline-2,2-dioxide;

3-(1'-hydroxy-2'-naphthyl)methylene-2,1-benzisothiazoline-2,2-dioxide;

3-(4'-hydroxy-2'-naphthyl)methylene-2,1-benzisothiazoline-2,2-dioxide;

3-(1',4'-dihydroxy-2'-naphthyl)methylene-2,1-benzisothiazoline-2,2-dioxide;

5-hydroxy-3-(2'-naphthyl)methylene-2,1-benzisothiazoline-2,2-dioxide;

5-hydroxy-3-(1'-hydroxy-2'-naphthyl)methylene-2,1-benzisothiazoline-2,2-dioxide;

5-hydroxy-3-(1'-hydroxy-2'-naphthyl)methylene-2,1-benzisothiazoline-2,2-dioxide;

5-hydroxy-3-(1',4'-dihydroxy-2'-naphthyl)methylene-2,1-benzisothiazoline-2,2-dioxide;

3-(5',6',7',8'-tetrahydronaphth-1'-yl)methylene-2,1-benzisothiazoline-2,2-dioxide;

3-(3'-hydroxy-5',6',7',8'-tetrahydronaphth-1'-yl)methylene-2,1-benzisothiazoline-2,2-dioxide;

3-(3'-hydroxy-5',6',7',8'-tetrahydronaphth-1'-yl)methylene-2,1-benzoisothiazoline-2,2-dioxide;

3-(3',4'-dihydroxy-5',6',7',8'-tetrahydronaphth-1'-yl)methylene-2,1-benzisothiazoline-2,2-dioxide;

3-(5',6',7',8'-tetrahydronaphth-2'-yl)methylene-2,1-benzisothiazoline-2,2-dioxide;

3-(1'-hydroxy-5',6',7',8'-tetrahydronaphth-2'-yl)methylene-2,1-benzisothiazoline-2,2-dioxide;

3-(4'-hydroxy-5',6',7',8'-tetrahydronaphth-2'-yl)methylene-2,1-benzisothiazoline-2,2-dioxide;

3-(1',4'-dihydroxy-5',6',7',8'-tetrahydronaphth-2'-yl)methylene-2,1-benzisothiazoline-2,2-dioxide;

3-(4'-quinolyl)methylene-2,1-benzisothiazoline-2,2-dioxide;

3-(8'-hydroxy-4'-quinolyl)methylene-2,1-benzisothiazoline-2,2-dioxide;

3-(7'-hydroxy-4'-quinolyl)methylene-2,1-benzisothiazoline-2,2-dioxide;

3-(7',8'-dihydroxy-4'-quinolyl)methylene-2,1-benzisothiazoline-2,2-dioxide;

3-(5'-quinolyl)methylene-2,1-benzisothiazoline-2,2-dioxide;

3-(8'-hydroxy-5'-quinolyl)methylene-2,1-benzisothiazoline-2,2-dioxide;

3-(7'-hydroxy-5'-quinolyl)methylene-2,1-benzisothiazoline-2,2-dioxide;

3-(7',8'-dihydroxy-5'-quinolyl)methylene-2,1-benzisothiazoline-2,2-dioxide;

5-hydroxy-3-(4'-quinolyl)methylene-2,1-benzisothiazoline-2,2-dioxide;

5-hydroxy-3-(8'-hydroxy-4'-quinolyl)methylene-2,1-benzisothiazoline-2,2-dioxide;

5-hydroxy-3-(7'-hydroxy-4'-quinolyl)methylene-2,1-benzisothiazoline-2,2-dioxide;

5-hydroxy-3-(7',8'-dihydroxy-4'-quinolyl)methylene-2,1-benzisothiazoline-2,2-dioxide;

5-hydroxy-3-(5'-quinolyl)methylene-2,1-benzisothiazoline-2,2-dioxide;

5-hydroxy-3-(8'-hydroxy-5'-quinolyl)methylene-2,1-benzisothiazoline-2,2-dioxide;

5-hydroxy-3-(7'-hydroxy-5'-quinolyl)methylene-2,1-benzisothiazoline-2,2-dioxide;

5-hydroxy-3-(7',8'-dihydroxy-5'-quinolyl)methylene-2,1-benzisothiazoline-2,2-dioxide;

3-(3'-indolyl)methylene-2,1-benzisothiazoline-2,2-dioxide;

3-(5'-hydroxy-3'-indolyl)methylene-2,1-benzisothiazoline-2,2-dioxide;

3(6'-hydroxy-3'-indolyl)methylene-2,1-benzisothiazoline-2,2-dioxide;

3-(5',6'-dihydroxy-3'-indolyl)methylene-2,1-benzisothiazoline-2,2-dioxide;

5-hydroxy-3-(3'-indolyl)methylene-2,1-benzisothiazoline-2,2-dioxide;

5-hydroxy-3-(5'-hydroxy-3'-indolyl)methylene-2,1-benzisothiazoline-2,2-dioxide;

5-hydroxy-3-(6'-hydroxy-3'-indolyl)methylene-2,1-benzisothiazoline-2,2-dioxide; and 5-hydroxy-3-(5',6'-dihydroxy-3'-indolyl)methylene-2,1-benzisothiazoline-2,2-dioxide;

which, when appropriate, may be either Z- or E-diastereoisomers or Z,E-mixtures of said diastereoisomers, or a pharmaceutically acceptable salt thereof.

The compounds of formula (I) and the salts thereof can be obtained by a process comprising the condensation of a compound of formula (II) or of formula (IIA), respectively

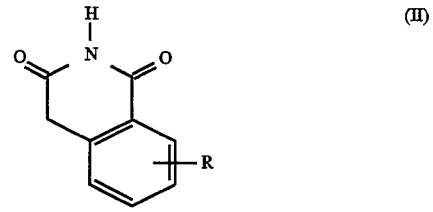

(II)

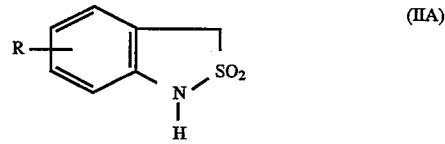

(IIA)

wherein R is as defined above, with an aldehyde of formula (III)

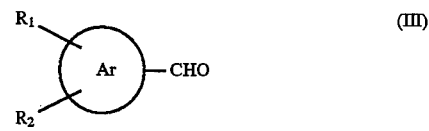

(III)

wherein Ar, $R_1$ and $R_2$ are as defined above; and, if desired, converting a compound of formula (I) into another compound of formula (I), and/or, if desired, converting a compound of formula (I) into a pharmaceutically acceptable salt thereof, and/or, if desired, separating a mixture of isomers of a compound of formula (I) into the single isomers.

In a compound of formula (III) each of the substituents —CHO, $R_1$ and $R_2$ may be independently on either of the aryl or heteroaryl moiety of the Ar group as naphthalene, quinoline or indole, and only the benzene moiety is preferably substituted when Ar is a tetrahydronaphthalene group. The preferred positions for R, R₁ and R₂ are as defined above for the compound of formula (I).

The condensation of a homophthalimide of formula (II) or of a 2,1-benzisothiazoline-2,2-dioxide of formula (IIA) with an aldehyde of formula (III) is an analogy process, which can be carried out according to known methods. Preferably said condensation can be performed in the presence of a basic catalyst, e.g. an organic base such as pyridine, or a suitable alkali metal hydroxide or alkoxide. For example, the reaction of a compound of formula (II) or (IIA) with a compound of formula (III) may be carried out under the conditions of the Knoevenagel reactions as described e.g. by G. Jones in Organic Reactions 15, 204 (1967).

Suitable catalysts are organic bases such as pyridine, piperidine or diethylamine. The condensation may be performed in an inert organic solvent e.g. pyridine, lower alkanol, e.g. methanol or ethanol, benzene or dioxane at temperatures ranging from about 0° C. to about 100° C. Preferably the reaction is carried out in warm ethanol solution in the presence of piperidine catalyst.

A compound of formula (I) can be converted into another compound of formula (I) according to known methods. For example the de-etherification of a compound of formula (I), wherein one or both of R and R₁ is $C_1$–$C_6$ alkoxy, so as to obtain a compound of formula (I) wherein one or both of R and R₁ is hydroxy, may be performed by well known methods in organic chemistry. For instance, in the case of a phenolic methyl ether the cleavage can be carried out for example with boron tribromide as described by J. F. N. McOmie in Tetrahedron 24, 2289 (1968). It is, in general, advisable to use about 1 mole of boron tribromide bromide for each ether group together with an extra mole of reagent for each group containing a potentially basic group. The reaction may be performed in an inert organic solvent such as dichloromethane, pentane or benzene under an inert atmosphere, e.g. nitrogen, at temperatures ranging from about −78° C. to about 29° C.

The acylation of a compound of formula (I), wherein R or R₁ or both are hydroxy, so as to obtain a compound of formula (I), wherein R or R₁ or both are acyloxy may be performed e.g. by reaction with a reactive derivative of a suitable carboxylic acid, such as an anhydride or halide, in the presence of a basic agent, at temperatures ranging from about 0° C. to about 50° C. Preferably the acylation is carried out by reaction with the respective anhydride in the presence of an organic base such as pyridine.

The optional salification of a compound of formula (i) as well as the conversion of a salt into the free compound and the separation of a mixture of isomers into the single isomers may be carried out by conventional methods. For example, the separation of a mixture of geometric isomers, e.g. Z- and E-isomers, may be carried out by fractional crystallization from a suitable solvent or by chromatography, either column chromatography or high pressure liquid chromatography.

The compounds of formula (II) can be prepared according to known methods from compounds of formula (IV)

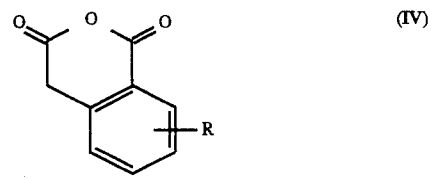

wherein R is as defined above. For example, according to the method described in Organic Synthesis Collective Volume I, 457 (2nd Edition), a homophthalic anhydride derivative can be fused together with ammonium carbonate, thus affording a compound of formula (II).

The compounds of formula (IIA) can be prepared according to known methods from compounds of formula (IVA)

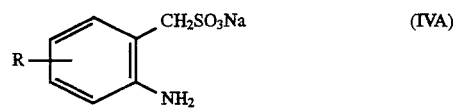

wherein R is as defined above. For example, according to the method described in J. Het. Chem. 23, 1645 (1986) a 2-aminobenzylsulfonic acid derivative in its sodium salt form is refluxed with phosphorous oxychloride thus affording a compound of formula (IIA).

The compound of formula (IVA) can be prepared by known methods from a compound of formula (VIA)

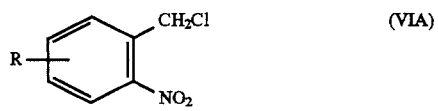

wherein R is as defined above. For example, according to the method described in DE-A-3309913 a 2-nitrobenzylchloride derivative can be treated with sodium sulfite to give the 2-nitrobenzylsulfonic acid derivative which subsequently is hydrogenated in the presence of a palladium catalyst thus affording a compound of formula (IVA).

The aldehydes of formula (III) are known or can be obtained according to well known methods.

For example, a 3-formylindole derivative of formula (III) can be obtained by formylation of a compound of formula (v)

wherein Ar is indole and R₁ and R₂ are as defined above, with N-methylformanilide and phosphorous oxychloride according to the well known Vilsmeyer-Haack method (for a review see W. G. Jackson et al. in J. Am. Chem. Soc. 103, 533 (1981)).

A compound of formula (III), when one or both of R₁ and R₂ is hydroxy, can be, for example, obtained according to the well known Reimer-Tiemann method. That is, a compound of formula (V) wherein one or both of R₁ and R₂ is hydroxy, can be treated with chloroform and alkali hydroxides in an aqueous or hydroalcoholic solution. —Another useful method for the synthesis of phenolaldehydes has been described scribed by H. Gross et al. in Chem. Ber. 96, 308 (1963) Accordingly a compound of formula (V) in which one or both of R₁ and R₂ is hydroxy can be treated with a dichloromethylether, e.g. dichloromethyl methyl ether, in the presence of a Friedel-Crafts catalyst such as titantetrachloride or aluminium trichloride in an inert solvent like dichloromethane of nitrobenzene at temperatures ranging from about 0° C. to about 60° C.

The compounds of formulae (IV), (IVA), (V) and (VIA) are known or can be obtained by known methods.

When in the new compounds of the present invention and in the intermediate products thereof groups are present which need to be protected before submitting them to the hereabove illustrated reactions, they may be protected before the reaction take place and then deprotected at the end of the reaction, according to well known methods in organic chemistry.

PHARMACOLOGY

The compounds of the invention possess specific tyrosine kinase inhibiting activity. It is believed that tyrosine kinase inhibitors may be of great importance in the control of uncontrolled cellular reproduction, i.e. in cellular reproduction disorders. Hence the compounds according to the present invention can be useful in the treatment of pathological proliferation disorders in mammals, including humans. Typical examples of such disorders are tumors, including leukemia, and psoriasis. They can also be useful in inhibiting the development of the athermatous plaque.

Recent studies on the molecular basis of neoplastic transformation have identified a family of genes, designed oncongenes, whose aberrant expression causes tumorigenesis. For example, the RNA tumor viruses possess such an oncogene sequence whose expression determines neoplastic conversion of infected cells. Several of their oncogene-encoded proteins, such as $pp60^{v-src}$, $p70^{gag-yes}$, $p130^{gag-fps}$ and $p70^{gag-fgr}$ display protein tyrosine kinase activity, that is they catalyse the transfer of the γ-phosphate from adenosine triphosphate (ATP) to tyrosine residues in protein substrate. In normal cells, several growth factor receptors, for example the receptors for PDGF, EGF, α-TGF and insulin, display tyrosine kinase activity.

Binding of the growth factor (GF) activates the receptor tyrosine kinase to undergo autophosphorylation and to phosphorylate closely adjacent molecules on tyrosine. Therefore, it is thought that the phosphorylation of these tyrosine kinase receptors plays an important role in signal transduction and that the principal function of tyrosine kinase activity in normal cells is to regulate cell growth. Perturbation of this activity by oncogenic tyrosine kinasesthat are either over-produced and/or display altered substrate specificity may cause loss of growth control and/or neoplastic transformation. Accordingly, a specific inhibitor of tyrosine kinases can be useful in investigating the mechanism of carcinogenesis, cell proliferation and differentiation and it can be effective in prevention and chemotherapy of cancer, and in other pathological proliferative conditions, for instance as mentioned above.

The tyrosine specific protein kinase activity of these compounds is shown e.g. by the fact that they are active in the in vitro test described herebelow.

Tyrosine kinase purification. The enzyme used in our test was the p45 v-abl tyrosine kinase which represents the catalytic domaine of the Abelson tyrosine kinase (isolated from the Abelson murine leukemia virus). The p45 v-abl kinase was produced and isolated as described by Wang et al. in J. Biol. Chem. 260, 64 (1985) and by Ferguson et al. in J. Biol. Chem. 260, 3652 (1985) and in Biochem. J. 257, 321 (1989).

Exogenous Substrate Kinase Assay. ($Val^5$)-Angiotensin II phosphorylation was performed by incubation with 40 ng of purified abl-kinase and $(γ-^{32}P)$-ATP, in 50 μl of buffer containing Tris-HCl 25 mM, pH 8.0, $MgCl_2$ 10 mM and dithiothreitol 0.1 mM (kinase buffer). The reaction mixture was incubated for the indicated time at 30° C. and the reaction stopped by adding 50 μl of 5% trichloroacetic acid.

After a brief incubation on ice, tubes were centrifuged. The supernatants were spotted on phosphocellulose paper squares (Whatman P-81) and washed extensively in acetic acid. The radioactivity bound to dried phosphocellulose squares was measured in a liquid scintillation counter. $IC_{50}$ values were calculated from triplicate determinations of each experimental point. Each inhibitor was tested at concentrations ranging from 0 to 400 μg in the presence of fixed concentrations of peptide (2 mM) and ATP (50 μM).

The activity data obtained for a representative group of compounds according to the present invention are set out in the following Table 1.

TABLE I

| p45 v-abl kinase inhibition | |
|---|---|
|  | $IC_{50}$ (μM) |
| 4-(4'-quinolyl)methylenehomophthalimide | 15 |
| 4-(4'-hydroxyphenyl)methylenehomophthalimide | 5 |
| 3-(4'-hydroxyphenyl)methylene-2,1-benz-isothiazoline-2,2-dioxide | 17 |
| 3-(3'-indolyl)methylene-2-,1-benzisothiazol-ine-2-dioxide | 113 |

In view of their high activity and low toxicity, the compounds of the invention can be used safely in medicine. For example, the approximate acute toxicity ($LD_{50}$) of the compounds of the invention in the mouse, determined by single administration of increasing doses and measured on the seventh day after the treatment was found to be negligible.

The compounds of the invention can be administered in a variety of dosage forms, e.g. orally, in the form of tablets, capsules, sugar or film coated tablets, liquid solutions or suspensions, rectally, in the form of suppositories; parenterally, e.g. intramuscularly, or by intravenous injection or infusion; or topically.

The dosage depends on the age, weight, condition of the patient and administration route; for example, the dosage adopted for oral administration to adult humans may range from about 10 to about 150–200 mg per dose, from 1 to 5 times daily. Of course, these dosage regimens may be adjusted to provide the optimal therapeutic response.

The invention includes pharmaceutical compositions comprising a compound of formula (IA) or a pharmaceutically acceptable salt thereof in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginares or sodium starch glycolate, effervescing mixtures; dyestuffs; sweeteners; wetting agents, such as lecithin, polysorbates, laurylsulphates; and, in general, non-toxic and pharmocologically inactive substances used in pharmaceutical formulations. Said pharmaceutical preparations may be manufactured in known manner, for example, by means of mixing, granulating, tabletting, sugar-coating or film-coating processes.

The liquid dispersion for oral administration may be e.g. syrups, emulsions and suspensions. The syrup may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusion may contain as carrier, for example, sterile water or, preferably, they may be in the form of sterile, aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin.

Compositions for topical application, e.g. creams, lotions, or pastes, can be prepared by admixing the active ingredient with a conventional oleaginous or emulsifying excipient.

A further object of the present invention is a combined method of treatment of cancer in mammals, including humans, in need of such treatment, said method comprising administering 1) a compound of formula (I), or a pharmaceutically acceptable salt thereof, and
2) an additional antitumor agent, in amounts and close enough together in time sufficient to produce a therapeutically useful effect.

Object of the present invention is also to provide products containing a compound of formula (I), or a pharmaceutically acceptable salt, and an additional antitumor agent as a combined preparation for simultaneous, separate or sequential use in anti-cancer therapy.

The term "antitumor agent" is meant to comprise both a single antitumor drug and "cocktails" i.e. a mixture of such drugs, according to the clinical practice. Antitumor agents that can be formulated with a compound of the invention or alternatively, can be administered in a combined method of treatment, are e.g. doxorubicin, daunomycin, epirubicin, idarubicin, etoposide, fluorouracil, mephalan, cyclophosphamide, bleomycin, vinblastin and mitomycin or a mixture of two or more thereof.

The compounds of the invention can therefore be used in a treatment to ameliorate a cancer. They may be administered to a patient suffering from a cancer treatable with an antitumor agent, for example an anthracycline glycoside such as doxorubicin, daunomycin, epirubicin or idarubicin as mentioned above, together with the antitumor agent. A compound of the invention and an antitumor agent such as an anthracycline glycoside can be administered to improve the condition of a patient having a leukaemia such as myeloblastic leukaemia, lymphoma, sarcoma, neuroblastoma, Wilm's tumor or malignant neoplasm of the bladder, breast, lung or thyroid.

The following examples illustrate but do not limit the invention:

EXAMPLE 1

To a solution of indole-3-carboxaldehyde (145 mg, 1 mmol) and 1,3-dihydro-2,1-benzisothiazoline-2,2-dioxide (203 mg, 1.2 mmol) in ethanol (15 ml) are added 5 drops of piperidine and the mixture is refluxed for 24 h. Then the mixture is evaporated under vacuum and the residue submitted to column chromatography using as eluants cyclohexane-ethyl acetate 70:30 and dichloromethane-methanol 100:5. Thus pure (E,Z)-3-(3'-indolyl)methylene-2,1-benzisothiazoline-2,2-dioxide is obtained in 65% yield (193 mg). $C_{16}H_{12}N_2O_2S$ calcd: C 64.85 H 4.08 N 9.45 S 10.82 found: C 64.55 H 4.01 N 9.35 S 10.55 MS (m/z): 296

NMR δ ppm: 6.74 (d,J=7.7 Hz, H-7), 6.99 (ddd, J=1.0, 7.7, 7.7 Hz, H-5), 7.20 (m, H-6, H-5', H-6'), 7.44 (m, H-7'), 7.85 (dd, J=1.0, 7.7 Hz, H-4), 8.00 (s, CH=), 8.20 (m, H-4'), 8.23 (d, J=3.0 Hz, H-2'), 10.73 (bs, NH-1), 11.93 (d, J=3.0 Hz, NH-1').

According to the above described procedure and starting from the appropriate compounds of formula (IIA) and (III) one can prepare the following compounds as single E- or Z-isomers, as well as their E,Z-mixtures:

(E,Z)-3-(4'-hydroxyphenyl)methylene-2,1-benzisothiazoline-2,2-dioxide MS (m/z) 273.

NMR δ ppm: 6.84 (d, J=8.7 Hz, H-3', H-5'), 7.66 (S, CH=), 7.78 (d, J=8.7 Hz, H-2', H-6'), 6.7–7.7 (m, H-4, H-5, H-6, H-7), 10.18 (S, OH), 10.80 (bs, NH).

3-phenylmethylene-2,1-benzisothiazoline-2,2-dioxide;

(3',4'-dihydroxyphenyl)methylene-2,1-benzisothiazoline-2,2-dioxide;

3(3'-hydroxyphenyl)methylene-2,1-benzisothiazoline-2,2-dioxide;

5-hydroxy-3-phenylmethylene-2,1-benzisothiazoline-2,2-dioxide;

5-hydroxy-3-(4'-hydroxyphenyl)methylene-2,1-benzisothiazoline-2,2-dioxide;

5hydroxy-3-(3'-hydroxyphenyl)methylene-2,1-benzisothiazoline-2,2-dioxide;

5-hydroxy-3-(3',4'-dihydroxyphenyl)methylene-2,1-benzisothiazoline-(2,2-dioxide;

3-(1'-naphthyl)methylene-2,1-benzisothiazoline-2,2-dioxide;

3-(3'-hydroxy-1'-naphthyl)methylene-2,1-benzisothiazoline-2,2-dioxide;

3-(4'-hydroxy-1'-naphthyl)methylene-2,1-benzisothiazoline-2,2-dioxide;

3-(3',4'-dihydroxy-1'-naphthyl)methylene-2,1-benzisothiazoline-2,2-dioxide;

5-hydroxy-3-(1'-naphthyl)methylene-2,1-benzisothiazoline-2,2-dioxide;

5-hydroxy-3-(3'-hydroxy-1'-naphthyl)methylene-2,1-benzisothiazoline-2,2-dioxide;

5-hydroxy-3-(4'-hydroxy-1'-naphthyl)methylene-2,1-benzisothiazoline-2,2-dioxide;

5-hydroxy-3-(3',4'-dihydroxy-1'-naphthyl)methylene-2,1-benzisothiazoline-2,2-dioxide;

3-(2'-naphthyl)methylene-2,1-benzisothiazoline-2,2-dioxide;

3-(1'-hydroxy-2'-naphthyl)methylene-2,1-benzisothiazoline-2,2-dioxide;

3(4'-hydroxy-2'-naphthyl)methylene-2,1-benzisothiazoline-2,2-dioxide;

3-(1',4'-dihydroxy-2'-naphthyl)methylene-2,1-benzisothiazoline-2,2-dioxide;

5-hydroxy-3-(2'-naphthyl)methylene-2,1-benzisothiazoline-2,2-dioxide;

5-hydroxy-3-(1'-hydroxy-2'-naphthyl)methylene-2,1-benzisothiazoline-2,2-dioxide;

5-hydroxy-3-(4'-hydroxy-2'-naphthyl)methylene-2,1-benzisothiazoline-2,2-dioxide;

5-hydroxy-3-(1',4'-dihydroxy-2'-naphthyl)methylene-2,1-benzisothiazoline-2,2-dioxide;

3-(5',6',7',8'-tetrahydronaphth-1'-yl)methylene-2,1-benzisothiazoline-2,2-dioxide;

3-(4'-hydroxy-5',6',7',8'-tetrahydronaphth-1'-yl)methylene-2,1-benzisothiazoline-2,2-dioxide;

3-(3'-hydroxy-5',6',7',8'-tetrahydronaphth-1'-yl)methylene-2,1-benzisothiazoline-2,2-dioxide;

3-(3',4'-dihydroxy-5',6',7',8'-tetrahydronaphth-1'-yl)methylene-2,1-benzisothiazoline-2,2-dioxide;

3-(5',6',7',8'-tetrahydronaphth-2'-yl)methylene 2,1-benzisothiazoline-2,2-dioxide;

3-(1'-hydroxy-5',6',7',8'-tetrahydronaphth-2'-yl)methylene-2,1-benzisothiazoline-2,2-dioxide;

3-(4'-hydroxy-5',6',7',8'-tetrahydronaphth-2'-yl)methylene-2,1-benzisothiazoline-2,2-dioxide;

3-(1',4'-dihydroxy-5',6',7',8'-tetrahydronaphth-2'-yl)methylene-2,1-benzisothiazoline-2,2-dioxide;

3-(4'-quinolyl)methylene-2,1-benzisothiazoline-2,2-dioxide;

3-(8'-hydroxy-4'-quinolyl)methylene-2,1-benzisothiazoline-2,2-dioxide;

3-(7'-hydroxy-4'-quinolyl)methylene-2,1-benzisothiazoline-2,2-dioxide;

3-(7',8'-dihydroxy-4'-quinolyl)methylene-2,1-benzisothiazoline-2,2-dioxide;

3-(5'-quinolyl)methylene-2,1-benzisothiazoline-2,2-dioxide;

3-(8'-hydroxy-5'-quinolyl)methylene-2,1-benzisothiazoline-2,2-dioxide;

3-(7'-hydroxy-5'-quinolyl)methylene-2,1-benzisothiazoline-2,2-dioxide;

3-(7',8'-dihydroxy-5'-quinolyl)methylene-2,1-benzisothiazoline-2,2-dioxide;

5-hydroxy-3-(4'-quinolyl)methylene-2,1-benzisothiazoline-2,2-dioxide;

5-hydroxy-3-(8'-hydroxy-4'-quinolyl)methylene-2,1-benzisothiazoline-2,2-dioxide;

5-hydroxy-3-(7'-hydroxy-4'-quinolyl)methylene-2,1-benzisothiazoline-2,2-dioxide;

5-hydroxy-3-(7',8'-dihydroxy-4'-quinolyl)methylene-2,1-benzisothiazoline-2,2-dioxide;

5-hydroxy-3-(5'-quinolyl)methylene-2,1-benzisothiazoline-2,2-dioxide;

5-hydroxy-3-(8'-hydroxy-5'-quinolyl)methylene-2,1-benzisothiazoline-2,2-dioxide;

5-hydroxy-3-(7'-hydroxy-5'-quinolyl)methylene-2,1-benzisothiazoline-2,2-dioxide;

5-hydroxy-3-(7',8'-dihydroxy-5'-quinolyl)methylene-2,1-benzisothiazoline-2,2-dioxide;

3-(5'-hydroxy-3'-indolyl)methylene-2,1-benzisothiazoline-2,2-dioxide;

3-(6'-hydroxy-3'-indolyl)methylene-2,1-benzisothiazoline-2,2-dioxide;

3-(5',6'-dihydroxy-3'-indolyl)methylene-2,1-benzisothiazoline-2,2-dioxide:

5-hydroxy-3-(3'-indolyl)methylene-2,1-benzisothiazoline-2,2-dioxide; -hydroxy-3-(5'-hydroxy-3'-indolyl)methylene-2,1-benzisothiazoline-2,2-dioxide;

5-hydroxy-3-(6'-hydroxy-3'-indolyl)methylene-2,1-benzisothiazoline-2,2-dioxide; and 5-hydroxy-3-(5',6'-dihydroxy-3'-indolyl)methylene-2,1-benzisothiazoline-2,2-dioxide.

EXAMPLE 2

The starting material for this de-etherification example is 3-(4'-methoxyphenyl)methylene-2,1-benzisothiazoline-2,2-dioxide, which can be obtained according to the procedure described in Example 1.

To a stirred solution of 3-(4'-methoxyphenyl)methylene-2,1-benzisothiazoline-2,2-dioxide (287 mg, 1 mmol) in anhydrous dichloromethane (10 ml) is added at −78° C. under nitrogen, over a period of 10 min, a 1.0M solution of boron tribromide in dichloromethane (3 ml, 3 mmol). The resulting mixture is stirred for another 1 h at −78° C. and then allowed to warm to room temperature. After stirring for 1.5 h at 20°–25° C. the mixture is cooled to −10° C. and then quenched by dropwise addition of water (10 ml) over a 10-min period. After addition of ethylacetate (10 ml) the organic layer is separated, washed with water, dried over $Na_2SO_4$ and evaporated under vacuum to dryness.

The residue is crystallized from ethanol thus giving pure 3-(4'-hydroxyphenyl)methylene-2,1-benzisothiazoline-2,2-dioxide (191 mg, 70% yield).

According to the above described procedure and starting from the corresponding phenolic methyl ether, the appropriate compounds mentioned in Example 1 can be obtained.

EXAMPLE 3

The starting material for this acylation example is 3-(4'-hydroxyphenyl)methylene-2,1-benzisothiazoline-2,1-dioxide, which may be obtained according to the procedure described in Example 1.

To a cooled solution of 3-(4'-hydroxyphenyl)methylene-2,1-benzisothiazoline-2,2-dioxide (273 mg, 1 mmol) in dry pyridine (0.5 ml) is added acetic anhydride (204 mg, 2 mmol) and the mixture maintained at 0°–5° C. overnight. Thereupon the mixture is concentrated under vacuum, the residue dissolved in dichloromethane, the organic layer washed with water and then evaporated under reduced pressure. The crude product is crystallized from chloroform-methanol to yield pure 3-(4'-acetoxyphenyl)methylene-2,1-benzisothiazoline-2,2-dioxide (80% yield). $C_{16}H_{13}NO_4S$ calcd: C 60.94 H 4.15 N 4.44 S 10.17 found: C 60.85 H 4.05 N 4.34 S 10.19 MS (m/z): 315

NMR δ ppm: 2.02 (S,OCOCH$_3$), 6.82 (d,J=8.7 Hz, H-3', H-5'), 7.66 (S,CH=), 7.76 (d,J=8.7 Hz, H-2', H-6'), 6.6–7.7 (m, H-4, H-5, H-6, H-7), 10.78 (bs, NH).

According to the above described procedure the phenols obtained in Example 1 can be transformed into the corresponding $C_2$–$C_6$ acyloxy compounds.

EXAMPLE 4

Here below we give an example for the preparation of a phenolaldehyde of general formula (III) from a phenol compound of general formula (V).

To a solution of 1,4-dihydroxy-5,6,7,8-tetrahydronaphthalene (164 mg, 1 mmol) in dichloromethane (5 ml) is added titantetrachloride (569 mg, 3 mmol). Then 1,1-dichlorodimethyl ether (173 mg, 1.5 mmol) is added dropwise under vigorous stirring and the reaction mixture stirred for another 3 h at room temperature. Finally hydrochloric acid 5% (1 ml) is added under ice-cooling. The organic phase is separated and the residual aqueous phase repeatedly extracted with ether. The combined organic phases are washed with saturated saline solution, dried over sodium sulfate and evaporated under vacuum. The residue is crystallized from benzene or alternatively submitted to flash chromatography on silica gel with benzene/ethylacetate 85:15 to afford pure 1,4-dihydroxy-5,6,7,8-tetrahydronaphthalene-2-carboxaldehyde in about 60% yield (108 mg).

mp 145° C. MS (m/z) 180.

NMR δ ppm: 10.4 (bs, OH), 9.7 (S, C$\underline{H}$O), 9.1 (bs, OH), 6.9 (S, H arom), 2.8 (m, H$_2$-5, H$_2$-8), 1.9 (m, H$_2$-6, H$_2$-7).

EXAMPLE 5

To a mixture of indole-3-carboxaldehyde (145 mg, 1 mmol) and homophthalimide (209 mg, 1.3 mmol) in ethanol (15 ml) are added few drops of piperidine as catalyst and the solution is refluxed for 5 h. Then water is added carefully and the resulting precipitate filtered off after cooling, washed with iced ethanol and dried under vacuum to give pure (E)-4-(3'-indolyl)-methylenehomophthalimide (245 mg, 85% yield). m.p.>250° C. MS (m/z) 288.

NMR δ ppm: 7.25 (m, H-6, H-7), 7.46 (m, H-5'), 7.33 (m, H-5'), 7.74 (m, H-6'), 8.09 (dd, J=1.4, 7.8 Hz, H-4'), 8.15 (m, H-8), 8.35 (d, J=8.1 Hz, H-7'), 8.50 (s,-C$\underline{H}$=C—CO) 9.25 (s, H-2'), 11.38, 12.20 (two bs, CON$\underline{H}$CO).

According to the above described procedure and starting from the appropriate compound of formulae (II) and (III) one can prepare the Following compounds as single E- or Z-isomers, as well as their E,Z-mixtures: (E,Z) -4-(4'-quinolyl)-methylenehomophthalimide, m.p. 245° C. MS (m/z) 300.

NMR δ ppm: 6.86 (d, J=7.8 Hz, H-5), 7.20 (m, H-6), 7.42 (m, H-7), 7.53 (dd, J=1.1, 4.4 Hz, H-3'), 7.58 (m, H-6'), 7.82 (m, H-7'), 7.88 (d, J=8.4 Hz, H-5'), 8.08 (dd, J=1.3, 8.0 Hz, H-8), 8.12 (d, J=8.6 Hz, H-8'), 8.40 (d, J=1.1 Hz, —C$\underline{H}$=C—CO—), 8.95 (d, J=4.4 Hz, H-2'), 11.81 (bs, CON$\underline{H}$CO). (E,Z)-4-(4'-hydroxyphenyl)methylenehomophthalimide, MS (m/z) 265.

NMR δ ppm: 7.15 (d, J=8.6 Hz, H-3', H-5'), 7.55 (d, J=8.6 Hz, H-2', H-6'), 8.07 (s, —C$\underline{H}$=C—CO, minor isomer), 8.48 (s, —CH=C—CO, major isomer), 12.46 (bs, OH), 13.28 (bs, NH, minor isomer), 13.39 (bs, NH, major isomer).

4-phenylmethylenehomophthalimide;
4-(3',4'-dihydroxyphenyl)methylenehomophthalimide;
4-(3'-hydroxyphenyl)methylenehomophthalimide;
6-hydroxy-4-phenylmethylenehomophthalimide;
6-hydroxy-4-(4'-hydroxyphenyl)methylenehomophthalimide;
6-hydroxy-4-(3'-hydroxyphenyl)methylenehomophthalimide;
6-hydroxy-4-(3',4'-dihydroxyphenyl)methylenehomophthalimide;
4-(1'-naphthyl)-methylenehomophthalimide;
4-(4'-hydroxy-1'-naphthyl)-methylenehomophthalimide;
4-(3'-hydroxy-1'-naphthyl)-methylenehomophthalimide;
4-(3',4'-dihydroxy-1'-naphthyl)-methylenehomophthalimide;
6-hydroxy-4-(1'-naphthyl)-methylenehomophthalimide;
6-hydroxy-4-(4'-hydroxy-1'-naphthyl)-methylenehomophthalimide;
6-hydroxy-4-(3'-hydroxy-1'-naphthyl)-methylenehomophthalimide;
6-hydroxy-4-(3',4'-dihydroxy-1'-naphthyl)-methylenehomophthalimide;
4-(2'-naphthyl)-methylenehomophthalimide;
4-(1'-hydroxy-2'-naphthyl)-methylenehomophthalimide;
4-(4'-hydroxy-2'-naphthyl)-methylenehomophthalimide;
4-(1',4'-dihydroxy-2'-naphthyl)-methylenehomophthalimide;
6-hydroxy-4-(2'-naphthyl)-methylenehomophthalimide;
6-hydroxy-4-(1'-hydroxy-2'-naphthyl)-methylenehomophthalimide;
6-hydroxy-4-(4'-hydroxy-2'-naphthyl)-methylenehomophthalimide;
6-hydroxy-4-(1',4'-dihydroxy-2'-naphthyl)-methylenehomophthalimide;
4-(1',4'-dihydroxy-5',6',7',8'-tetrahydronaphth-2'-yl) methylene homophthalimide (70% yield). C$_{20}$H$_{17}$NO$_4$ requires: C 7.63 H 5.11 N 4.18 found: C 71.45 H 5.05 N 4.05 MS m/z: 335
4-(5',6',7',8'-tetrahydronaphth-1'-yl)-methylenehomophthalimide;
4-(4'-hydroxy-5',6',7',8'-tetrahydronaphth-3'-yl)-methylenehomophthalimide;
4-(8'-hydroxy-5',6',7',8'-tetrahydronaphth-1'-yl)-methylenehomophthalimide;
4-(3',4'-dihydroxy-5',6',7',8'-tetrahydronaphth-1'-yl)-methylenehomophthalimide;
6-hydroxy-4-(5',6',7',8'-tetrahydronaphth-1'-yl)methylenehomophthalimide;
6-hydroxy-4-(4'-hydroxy-5',6',7',8'-tetrahydronaphth-1'-yl)-methylenehomophthalimide;
6-hydroxy-4-(3'-hydroxy-5',6',7',8'-tetrahydronapth-1'-yl)-methylenehomophthalimide;
4-hydroxy-4-(3',4'-dihydroxy-5',6',7',8'-tetrahydronaphth-1'-yl)-methylenehomophthalimide;
4-(5',6,7',8'-tetrahydronaphth-2'-yl)-methylenehomophthalimide;
4-(1'-hydroxy-5',6',7',8'-tetrahydronaphth-2'-yl)-methylenehomophthalimide;
4-(4'-hydroxy-5',6',7',8'-tetrahydronaphth-2'-yl)-methylenehomophthalimide;
6-hydroxy-4-(5',6',7',8'-tetrahydronaphth-2'-yl)-methylenehomophthalimide;
6-hydroxy-4-(1'-hydroxy-5',6',7',8'-tetrahydronaphth-2'-yl)-methylenehomophthalimide;
6-hydroxy-4-(4'-hydroxy-5',6',7',8'-tetrahydronaphth-1'-yl)-methylenehomophthalimide; and
6-hydroxy-4-(1',4'-dihydroxy-5',6',7',8'-tetrahydronaphth-2'-yl)-methylenehomophthalimide.
4-(8'-hydroxy-4'-quinolyl)-methylenehomophthalimide;
4-(7'-hydroxy-4'-quinolyl)-methylenehomophthalimide;
4-(7',8'-dihydroxy-4'-quinolyl)-methylenehomophthalimide;
6-hydroxy-4-(4'-quinolyl)-methylenehomophthalimide;
6-hydroxy-4-(8'-hydroxy-4'-quinolyl)-methylenehomophthalimide;
6-hydroxy-4-(7'-hydroxy-4'-quinolyl)-methylenehomophthalimide;
4-hydroxy-4-(7',8'-dihydroxy-4'-quinolyl)-methylenehomophthalimide;
4-(5'-quinolyl)methylenehomophthalimide;
4-(8'-hydroxy-5'-quinolyl)-methylenehomophthalimide;
4-(7'-hydroxy-5'-quinolyl)-methylenehomophthalimide;
4-(7',8'-dihydroxy-5'-quinolyl)-methylenehomophthalimide;

6-hydroxy-4-(5'-quinolyl)-methylenehomophthalimide;

6-hydroxy-4-(8'-hydroxy-5'-quinolyl)-methylenehomophthalimide;

6-hydroxy-4-(7'-hydroxy-5'-quinolyl)-methylenehomophthalimide;

6-hydroxy-4-(7',8'-dihydroxy-5'-quinolyl)-methylenehomophthalimide;

4-(5'-hydroxy-3'-indolyl)-methylenehomophthalimide;

4-(6'-hydroxy-3'-indolyl)-methylenehomophthalimide;

4-(5',6'-dihydroxy-3'-indolyl)-methylenehomophthalimide;

6-hydroxy-4-(3'-indolyl)-methylenehomophthalimide;

6-hydroxy-4-(5'-hydroxy-3'-indolyl)-methylenehomophthalimide;

6-hydroxy-4-(6'-hydroxy-3'-indolyl)-methylenehomophthalimide; and 6-hydroxy-4-(5',6'-dihydroxy-3'-indolyl)-methylenehomophthalimide.

EXAMPLE 6

The starting material for this de-etherification example is 4-(4'-methoxyphenyl)methylenehomophthalimide, which can be obtained according to the procedure described in Example 5.

To a stirred solution of 4-(4'-methoxyphenyl) methylenehomophthalimide (279 mg, 1 mmol) in anhydrous dichloromethane (10 ml) is added at −78° C. under nitrogen, over a period of 10 min, a 1.0M solution of boron tribromide in dichloromethane (3 ml, 3 mmol). The resulting mixture is stirred for another 1 h at −78° C. and then allowed to warm to room temperature. After stirring for 1.5 h at 20°–25° C. the mixture is cooled to −10° C. and then quenched by dropwise addition of water (10 ml) over a 10-min period. After addition of ethyl acetate (10 ml) the organic layer is separated, washed with water, dried over $Na_2SO_4$ and evaporated under vacuum to dryness. The residue is crystallized from ethanol thus giving pure 4-(4'-hydroxyphenyl) methylenehomophthalimide (186 mg, yield 70%).

According to the above described procedure and starting from the corresponding phenolic methylether, all the compounds pounds of the invention mentioned in Example 5 can be obtained.

EXAMPLE 7

In the following, an illustrative example is given for the preparation of a homophthalimide of general formula (II) from the corresponding homophthalic arthydride of general formula (IV).

Homophthalic sunhydride (1.62 g, 10 mmol) and ammonium carbonate (1.61 g, 10 mmol) are ground in a mortar and then slowly heated to fusion at about 280° C. After 2 h, the reaction mixture is allowed to cool. The product is practically pure and needs no further treatment. Thus homophthalimide is obtained in 95% yield (153 mg).

m.p. 223°–233° C. MS (m/z) 161.

NMR δ ppm: 4.02 (s, $CH_2CO$), 7.37 (d, J=7.7 Hz, H-5), 7.44 (m, H-7), 7.64 (m, H-6), 8.00 (dd, J=1.3, 7.8 Hz, H-8), 11.29 (bs, NH).

EXAMPLE 8

Tablets each weighing 0.150 g and containing 25 mg of the active substance, were manufactured as follows:

| Composition (for 10,000 tablets) | |
|---|---|
| 4-(3'-indolyl)methylenehomophthalimide | 250 g |
| Lactose | 800 g |
| Corn starch | 415 g |
| Talc powder | 30 g |
| Magnesium stearate | 5 g |

The 4-(3'-indolyl)methylenehomophthalimide, the lactose and half the corn starch were mixed; the mixture was then forced through a sieve of 0.5 mm mesh size. Corn starch (10 g) was suspended in warm water (90 ml) and the resulting paste was used to granulate the powder.

The granulate was dried, comminuted on a sieve of 1.4 mm mesh size, then the remaining quantity of starch, talc and magnesium stearate was added, carefully mixed and processed into tablets.

EXAMPLE 9

Capsules, each dosed at 0.200 g and containing 20 mg of the active substance were prepared.

| Composition for 500 capsules: | |
|---|---|
| 4-(4'-quinolyl)methylenehomophthalimide | 10 g |
| Lactose | 80 g |
| Corn starch | 5 g |
| Magnesium stearate | 5 g |

This formulation was encapsulated in two-piece hard gelatin capsules and dosed at 0.200 g for each capsule.

EXAMPLE 10

Tablets each weighing 0.150 g and containing 25 mg of the active substance, can be manufactured as follows: composition (for 10000 tablets):

| composition (for 10000 tablets): | |
|---|---|
| 3-(3'-indolyl)methylene-2,1-benziso-thiazoline-2,2-dioxide | 250 g |
| Lactose | 800 g |
| Corn starch | 415 g |
| Talc powder | 30 g |
| Magnesium stearate | 5 g |

The 3-(8'-indolyl)methylene-2,1-benzisothiazoline-2,2-dioxide, the lactose and half the corn starch are mixed; the mixture is then forced through a sieve of 0.5 mm mesh size.

Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added, carefully mixed and processed into tablets.

EXAMPLE 11

Capsules, each dosed at 0.200 g and containing 20 mg of the active substance can be prepared.

| Composition for 500 capsules: | |
|---|---|
| 3-(4'-hydroxyphenyl)methylene-2,1-benzisothiazoline-2,2-dioxide | 10 g |

-continued

Composition for 500 capsules:

| | |
|---|---|
| Lactose | 80 g |
| Corn starch | 5 g |
| Magnesium stearate | 5 g |

This formulation is encapsulated in two-piece hard gelatin capsules and dosed at 0.200 for each capsule.

We claim:

1. A compound of formula (I)

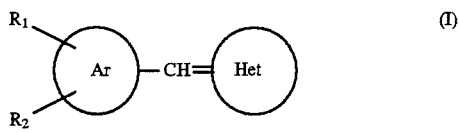

wherein

Ar is mono-or bicyclic ring system chosen from benzene, naphthalene, and 5,6,7,8 tetrahydronaphthalene;

Het is

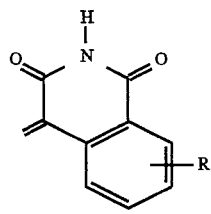

R is hydrogen, or, hydroxy;

$R_1$ is hydrogen, or hydroxy;

$R_2$ is hydrogen, or hydroxy; or the pharmaceutically acceptable salt thereof, and wherein the (Ar) $R_1$ $R_2$ group represents unsubstituted phenyl then R is other than hydrogen.

2. A compound selected from 4-(4'-hydroxyphenyl)methylenehomophthalimide;
4-(3',4'-dihydroxyphenyl)methylenehomophthalimide;
4-(3'-hydroxyphenyl)methylenehomophthalimide;
6-hydroxy-4-phenylmethylenehomophthalimide;
6-hydroxy-4-(4'-hydroxyphenyl) methylenehomophthalimide;
6-hydroxy-4-(3'-hydroxyphenyl) methylenehomophthalimide;
6-hydroxy-4-(3',4'-dihydroxyphenyl) methylenehomophthalimide;
4-(1'-naphthyl)-methylenehomophthalimide;
4-(4'-hydroxy-1'-naphthyl)-methylenehomophthalimide;
4-(3'-hydroxy-1'-naphthyl)-methylenehomophthalimide;
4-(3',4'-dihydroxy-1'-naphthyl)-methylenehomophthalimide;
6-hydroxy-4-(1'-naphthyl)-methylenehomophthalimide;
6-hydroxy-4-(4'-hydroxy-1'-naphthyl)-methylenehomophthalimide;
6-hydroxy-4-(3'-hydroxy-1'-naphthyl)-methylenehomophthalimide;
6-hydroxy-4-(3',4'-dihydroxy-1'-naphthyl)-methylenehomophthalimide;
4-(2'-naphthyl)-methylenehomophthalimide;
4-(1'-hydroxy-2'-naphthyl)-methylenehomophthalimide;
4-(4'-hydroxy-2'-naphthyl)-methylenehomophthalimide;
4-(1',4'-dihydroxy-2'-naphthyl)-methylenehomophthalimide;
6-hydroxy-4-(2'-naphthyl)-methylenehomophthalimide;
6-hydroxy-4-(1'-hydroxy-2'-naphthyl)-methylenehomophthalimide;
6-hydroxy-4-(4'-hydroxy-2'-naphthyl)-methylenehomophthalimide;
6-hydroxy-4-(1',4'-dihydroxy-2'-naphthyl)-methylenehomophthalimide;
4-(5',6',7',8'-tetrahydronaphth-1'-yl)-methylenehomophthalimide;
4-(4'-hydroxy-5',6',7',8'-tetrahydronaphth-1'-yl)-methylenehomophthalimide;
4-(3'-hydroxy-5',6',7',8'-tetrahydronaphth-1'-yl)-methylenehomophthalimide;
4-(3',4'-dihydroxy-5',6',7',8'-tetrahydronaphth-1'-yl)-methylenehomophthalimide;
6-hydroxy-4-(5',6',7',8'-tetrahydronaphth-1'-yl)-methylenehomophthalimide;
6-hydroxy-4-(4'-hydroxy-5',6',7',8'-tetrahydronaphth-1'-yl)-methylenehomophthalimide;
6-hydroxy-4-(3'-hydroxy-5',6',7',8'-tetrahydronaphth-1'-yl)-methylenehomophthalimide;
6-hydroxy-4-(3',4'-dihydroxy-5',6',7',8'-tetrahydronaphth-1-yl)-methylenehomophthalimide;
4-(5',6',7',8'-tetrahydronaphth-2'-yl)-methylenehomophthalimide;
4-(1'-hydroxy-5',6',7',8'-tetrahydronaphth-2'-yl)-methylenehomophthalimide;
4-(4'-hydroxy-5',6',7',8'-tetrahydronaphth-2'-yl)-methylenehomophthalimide;
4-(1',4'-dihydroxy-5',6',7',8'-tetrahydronaphth-2'-yl) ethylenehmophthalimide;
6-hydroxy-4-(5',6',7',8'-tetrahydronaphth-2'-yl)-methylenehomophthalimide;
6-hydroxy-4-(1'-hydroxy-5',6',7',8'-tetrahydronaphth-2'-yl)-methylenehomophthalimide;
6-hydroxy-4-(4'-hydroxy-5',6',7',8'-tetrahydronaphth-2'-yl)-methylenehomophthalimide; and
6-hydroxy-4-(1',4'-dihydroxy-5',6',7',8'-tetrahydronaphth-2'yl)-methylenehomopthalimide;
which, when appropriate, the compounds may be either Z- or E-diastereoisomers or Z, E mixtures of said diastereoisomers, or the pharmaceutically acceptable salts thereof.

3. A pharmaceutical composition comprising a pharmaceutically acceptable carrier and/or diluent and, as active principle, a compound of general formula (IA)

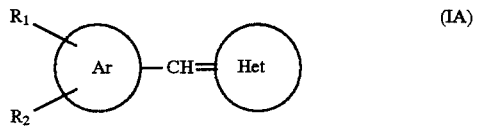

wherein

Ar is mono-or bicyclic ring system chosen from benzene, naphthalene, and 5,6,7,8 tetrahydronaphthalene;

Het is

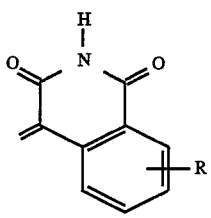

R is hydrogen, or, hydroxy;

$R_1$ is hydrogen or hydroxy;

$R_2$ is hydrogen, or, hydroxy; or a pharmaceutically acceptable salt thereof.

4. A pharmaceutical composition comprising a pharmaceutically acceptable carrier and/or diluent and, as active principle, a compound selected from 4-phenylmethylenehomophthalimide;

4-(4'-hydroxyphenyl)methylenehomophthalamide;
4-(3',4'-dihydroxyphenyl)methylenehomopphthalimide;
4-(3'-hydroxyphenyl)methylenehomophthalimide;
6-hydroxy-4-phenylmethylenehomophthalimide;
6-hydroxy-4-(4'-hydroxyphenyl)methylenehomophthalimide;
6-hydroxy-4-(3'-hydroxyphenyl)methylenehomophthalimide;
6-hydroxy-4-(3',4'-dihydroxyphenyl)methylenehomophthalimide;
4-(1'-naphthyl)-methylenehomophthalimide;
4-(4'-hydroxy-1'-naphthyl)-methylenehomophthalimide;
4-(3'-hydroxy-1'-naphthyl)-methylenehomophthalimide;
4-(3',4'-dihydroxy-1'-naphthyl)-methylenehomophthalimide;
6-hydroxy-4-(1'-naphthyl)-methylenehomophthalimide;
6-hydroxy-4-(4'-hydroxy-1'-naphthyl)-methylenehomophthalimide;
6-hydroxy-4-(3'-hydroxy-1'-naphthyl)-methylenehomophthalimide;
6-hydroxy-4-(3',4'-dihydroxy-1'-naphthyl)-methylenehomophthalimide;
4-(2'-naphthyl)-methylenehomophthalimide;
4-(1'-hydroxy-2'-naphthyl)-methylenehomophthalimide;
4-(4'-hydroxy-2'-naphthyl)-methylenehomophthalimide;
4-(1',4'-dihydroxy-2'-naphthyl)-methylenehomophthalimide;
6-hydroxy-4-(2'-naphthyl)-methylenehomophthalimide;
6-hydroxy-4-(1'-hydroxy-2'-naphthyl)-methylenehomophthalimide;
6-hydroxy-4-(4'-hydroxy-2'-naphthyl)-methylenehomophthalimide;
6-hydroxy-4-(1',4'-dihydroxy-2'-naphthyl)-methylenehomophthalimide;
4-(5',6',7',8'-tetrahydronaphth-1'-yl)-methylenehomophthalimide;
4-(4'-hydroxy-5',6',7',8'-tetrahydronaphth-1'-yl)-methylenehomophthalimide;
4-(3'-hydroxy-5',6',7',8'-tetrahydronapth-1'-yl)-methylenehomophthalamide;
4-(3',4'-dihydroxy-5',6',7,8'-tetrahydronaphth-1'-yl)-methylenehomophthalimide;
6-hydroxy-4-(5',6',7',8'-tetrahydronaphth-1'-yl)-methylenehomophthalimide;
6-hydroxy-4-(4'-hydroxy-5',6',7',8'-tetrahydronaphth-1'-yl)-methylenenomophthalamide;
6-hydroxy-4-(3'-hydroxy-5',6',7',8'-tetrahydronaphth-1'-yl)-methylenehomophthalimide;
6-hydroxy-4-(3',4'-dihydroxy-5',6',7',8'-tetrahydronaphth-1'-yl)-methylenehomophthalimide;
4-(5',6',7',8'-tetrahydronaphth-2'-yl)-methylenehomopnthalimide;
4-(1'-hydroxy-5',6',7',8'-tetrahydronaphth-2'-yl)-methylenehomophthalimide;
4-(4'-hydroxy-5',6',7',8'-tetrahydronaphth-2'-yl)-methylenehomophthalimide;
4-(1',4'-dihydroxy-5',6',7',8'-tetrahydronaphth-2'-yl)-methylenehomophthalimide;
6-hydroxy-4-(5',6',7',8'-tetrahydronaphth-2'-yl)-methylenehomophthalimide;
6-hydroxy-4-(1'-hydroxy-5',6',7',8'-tetrahydronaphth-2'-yl)methylenehomophthalimide;
6-hydroxy-4-(1',4'-hydroxy-5',6',7',8'-tetrahydronaphth-2'-yl)-methylenehomophthalimide; and
6-hydroxy-4-(1',4'-dihydroxy-5',6',7',8'-tetrahydronaphth-2'-yl)methylenehomophthalimide;

which, when appropriate, the compounds may be either Z- or E-diastereoisomers or Z, E-mixtures of said diastereoisomers, or a pharmaceutically acceptable salt thereof.

5. A pharmaceutical composition comprising a pharmaceutically acceptable carrier and/or diluent and, as active principle, a compound of formula (I) or a pharmaceutically acceptable salt thereof as claimed in claim 1.

6. A compound of formula (I)

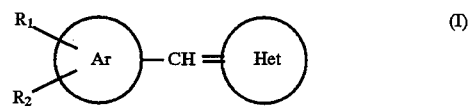

wherein

Ar is a mono- or bicyclic ring system chosen from benzene, naphthalene and tetrahydronaphthalene, Het is

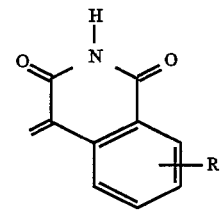

R is hydrogen, halogen, hydroxy, $C_1$–$C_6$ alkoxy, $C_2$–$C_6$ acyloxy, cyano, nitro, amino or —$COOR_3$ in which $R_3$ is hydrogen or $C_1$–$C_6$ alkyl;

$R_1$ is hydroxy, $C_2$–$C_6$ acyloxy, cyano, nitro or —$COOR_3$ in which $R_3$ is as defined above;

$R_2$ is hydrogen, halogen, hydroxy or $C_1$–$C_6$ alkyl;

or its pharmaceutically acceptable salt, and wherein when at the same time the (Ar)$R_1R_2$ group represents 4-cyano-phenyl and Het is a 4-homophthalimide group then R is other than hydrogen.

7. A pharmaceutical composition comprising a pharmaceutically acceptable carrier and/or diluent and, as active principle, a compound of general formula (IA)

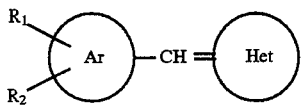
(IA)

wherein

Ar is a mono- or bicyclic ring system chosen from benzene, naphthalene and tetrahydronaphthalene, Het is

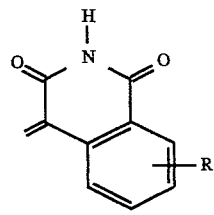

R is hydrogen, halogen, hydroxy, $C_1-C_6$ alkoxy, $C_2-C_6$ acyloxy, cyano, nitro, amino or —$COOR_3$ in which $R_3$ is hydrogen or $C_1-C_6$ alkyl;

$R_1$ is hydroxy, $C_2-C_6$ acyloxy, cyano, nitro or —$COOR_3$ in which $R_3$ is as defined above;

$R_2$ is hydrogen, halogen, hydroxy or $C_1-C_6$ alkyl; or a pharmaceutically acceptable salt thereof.

8. A pharmaceutical composition comprising a pharmaceutically acceptable carrier and/or diluent and, as active principle, a compound of general formula (IA)

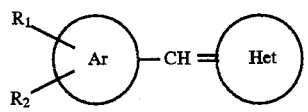
(IA)

wherein

Ar is a mono- or bicyclic ring system chosen from benzene, naphthalene and tetrahydronaphthalene, Het is

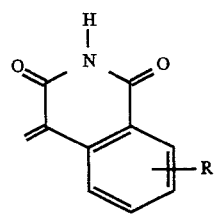

R is hydrogen, halogen, hydroxy, $C_1-C_6$ alkoxy, $C_2-C_6$ acyloxy, cyano, nitro, amino or —$COOR_3$ in which $R_3$ is hydrogen or $C_1-C_6$ alkyl;

$R_1$ is hydrogen or $C_1-C_6$ alkyl;

$R_2$ is hydrogen, halogen, hydroxy or $C_1-C_6$ alkyl; or a pharmaceutically acceptable salt thereof.

9. A compound of formula (I) according to claim 1, wherein Ar is naphthalene and R, $R_1$ and $R_2$ all are hydroxy.

* * * * *